United States Patent [19]

Comins

[11] Patent Number: 5,395,939
[45] Date of Patent: Mar. 7, 1995

[54] METHOD OF MAKING ASYMMETRIC DE RING INTERMEDIATES FOR THE SYNTHESIS OF CAMPTOTHECIN AND CAMPTOTHECIN ANALOGS

[75] Inventor: Daniel L. Comins, Cary, N.C.

[73] Assignee: North Carolina State University, Raleigh, N.C.

[21] Appl. No.: 159,117

[22] Filed: Nov. 30, 1993

[51] Int. Cl.⁶ ............... C07D 491/056; C07D 491/06
[52] U.S. Cl. ............................................. 546/115
[58] Field of Search ........................................... 546/115

[56] References Cited

U.S. PATENT DOCUMENTS

| | | | |
|---|---|---|---|
| 4,011,231 | 3/1977 | Carroll | 546/115 |
| 4,031,108 | 6/1977 | Nakanishi | 546/115 |
| 4,477,671 | 10/1984 | Cue | 546/291 |
| 4,610,990 | 9/1986 | Esanu | 514/302 |
| 4,713,458 | 12/1987 | Frazier | 546/115 |
| 5,162,532 | 11/1992 | Comins et al. | 546/48 |
| 5,212,317 | 5/1993 | Comins et al. | 546/301 |
| 5,342,947 | 8/1994 | Lackey et al. | 546/41 |

OTHER PUBLICATIONS

Daniel L. Comins, et al., A 10-Step Asymetric Synthesis of (S)-Camptothecin, *Journal of the American Chemical Society*, pp. 10971–10972, 1992.

*Primary Examiner*—C. Warren Ivy
*Assistant Examiner*—D. Margaret M. Mach
*Attorney, Agent, or Firm*—Bell, Seltzer, Park & Gibson

[57] ABSTRACT

Methods of making asymmetric DE ring intermediates for the synthesis of camptothecin and camptothecin analogs employ a dioxane intermediate as the immediate precursor to the DE ring intermediate. Novel intermediates are also disclosed.

7 Claims, No Drawings

METHOD OF MAKING ASYMMETRIC DE RING INTERMEDIATES FOR THE SYNTHESIS OF CAMPTOTHECIN AND CAMPTOTHECIN ANALOGS

FIELD OF THE INVENTION

The present invention provides methods for making asymmetric DE ring intermediates in optically pure form via dioxane intermediates.

BACKGROUND OF THE INVENTION

Camptothecin (Chem. Abstracts Registry No. 7689-03-4) is a naturally occurring compound found in *Camptotheca acuminata* (Nyssaceae) which has antileukemic and antitumor properties. Numerous camptothecin analogs having like properties are known, examples being those described in U.S. Pat. No. 4,894,456 to Wall et al. and European Patent Application No. 0 325 247 of Yaegashi et al.

A number of syntheses for camptothecin are known. Several routes are reviewed in *Natural Products Chemistry*, Vol. 2, 358-361 (K. Nakanishi, T. Goto, S. Itô, S. Natori and S. Nozoe eds.) and in J. Cai and C. Hutchinson, Camptothecin, in *The Alkaloids*, Vol. XXI, 101-137 (Academic Press 1983). The biosynthesis of camptothecin is described in *Natural Products Chemistry*, Vol. 3, 573-574 (K. Nakanishi et al. eds.). One synthetic route is described in U.S. Pat. No. 4,894,456 to Wall et al.

U.S. Pat. No. 5,162,532 to Comins and Baevsky describes a parallel synthesis for camptothecin and camptothecin analogs, where compounds of Formula I are prepared by scheme A:

Scheme A

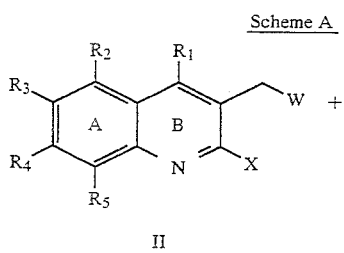

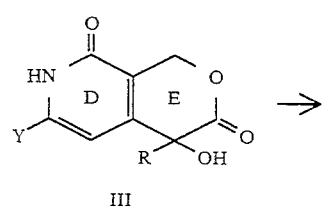

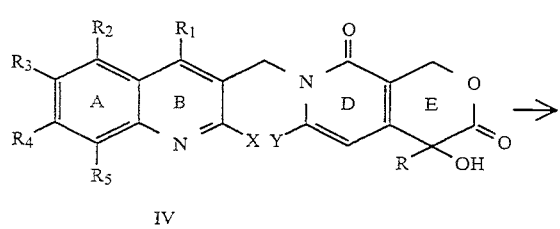

-continued
Scheme A

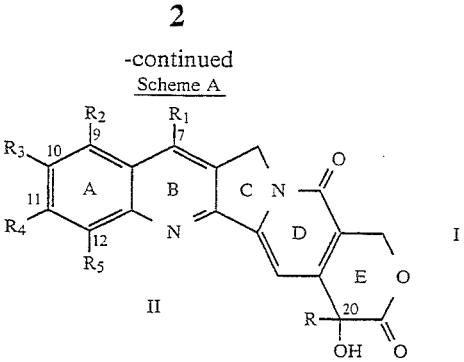

In U.S. Pat. No. 5, 212,317 to Comins and Baevsky, compounds of Formula III in scheme A above are prepared in asymmetric form in accordance with scheme C below:

Scheme C

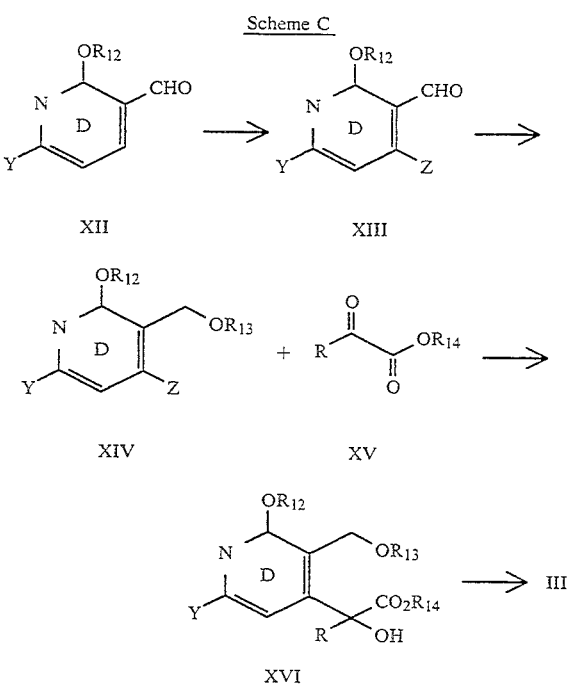

An object of the present invention is to provide new methods for preparing compounds of Formula III above and useful for making such compounds, all of which are useful for the synthesis of camptothecin and camptothecin analogs.

SUMMARY OF THE INVENTION

The present invent ion provides methods and intermediates for preparing optically pure forms of the compounds of Formula III:

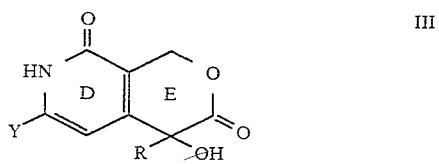

wherein R is lower alkyl and Y is H or halogen, preferably Cl.

In one embodiment, illustrated by Scheme D,

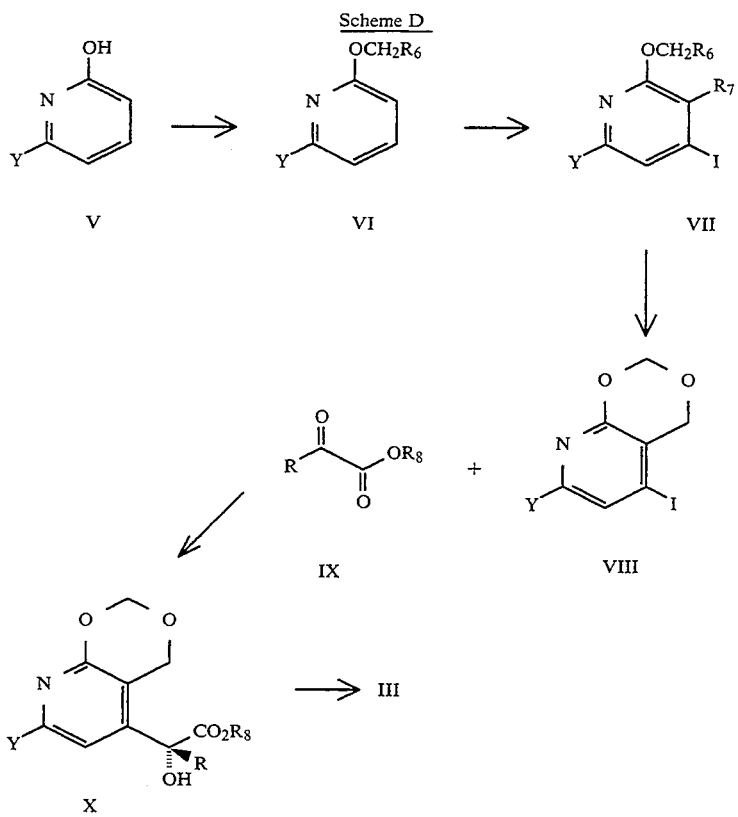

$R_8$ is optically pure, which can lead to a diastereomerically enhanced compound X and optically pure compound of Formula III.

DETAILED DESCRIPTION OF THE INVENTION

As used herein, the term "loweralkyl" means a linear or branched alkyl group with 1–8, preferably 1–4 carbon atoms, such as methyl, ethyl, propyl, isopropyl, n-butyl, tert-butyl, hexyl, and octyl. This definition also applies to a loweralkyl moiety in the loweralkoxy, lower alkylthio, and di(loweralkyl)amino groups. Thus, examples of loweralkyoxy groups are methoxy, ethoxy, propoxy, secbutoxy, and isohexoxy; examples of loweralkylthio groups are methylthio, ethylthio, tert-butylthio, and hexylthio; and examples of di(loweralkyl)amino groups are dimethylamino, diethylamino, diisopropylamino, di(n-butyl)amino, and dipentylamino.

The terms "halo" and "halogen" as used herein refers to a substituent which may be fluoro, chloro, bromo, or iodo.

The compounds of Formula III above are, as noted above, prepared according to Scheme D below,

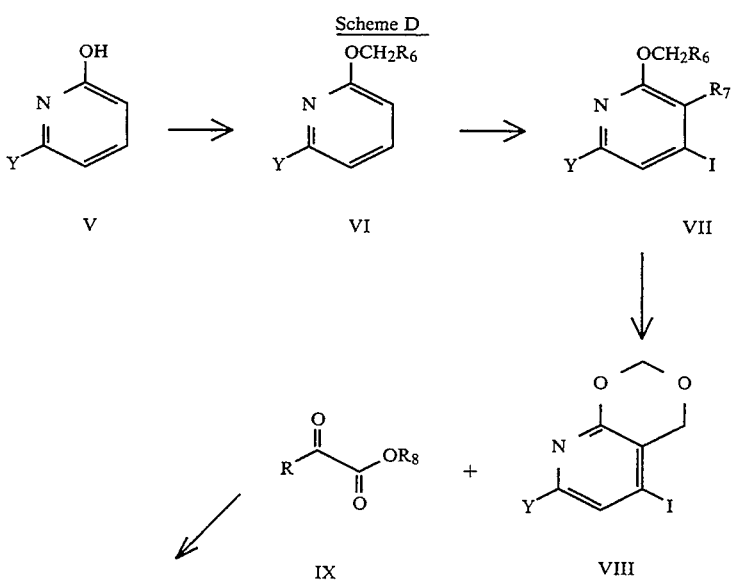

Scheme D

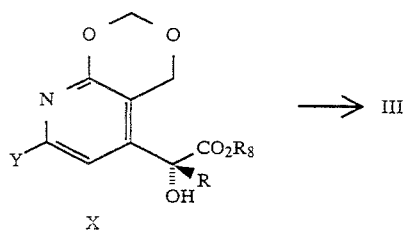

→ III wherein R, and Y are as given in connection with Formula III above, $R_6$ is lower alkoxy and $R_7$ is lower hydroxy-alkyl. $R_8$ can be any chiral moiety which, because of its geometric configuration, directs the nucleophilic substitution of compound VIII by compound IX to preferentially form the tertiary alcohol of compound X in one stereochemical orientation over its opposite stereochemical orientation. $R_8$ forces a preferential formation of compound X by sterically hindering the competing formation of the nonpreferred diastereomer. Exemplary chiral compounds suitable for use in the process include aryl and alkyl aryl compounds optionally substituted from 1 to 5 times with $C_1$–$C_4$ alkyl groups, any of the compounds disclosed in U.S. Pat. No. 5,262,571 issued 16 November 1993, the subject matter of which is herein incorporated by reference, 4-phenyl-methyl-2-oxazolidine, 3-(1-naphthyl)-4,7,7-trimethyl-bicyclo [2.2.1]heptane, trans-2,5 Bis(methoxymethoxymethyl)pyrrolidine, 2,10-camphorsulfamide, proline benzyl ester, pantolactone, and 4-benzyl-Z-oxazolidinone. Preferred chiral auxiliaries are compounds of Formula

XI

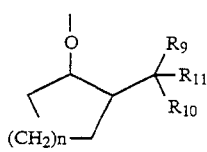

wherein n is 1, 2, or 3, $R_9$ is a $C_1$–$C_4$ alkyl group and $R_{10}$ is the same as $R_9$, or $R_9$ and $R_{10}$ together form cyclopentane or cyclohexane, and $R_{11}$ is selected from the group consisting of phenyl, naphthyl, anthryl, and phenanthryl optionally substituted 1 to 5 times with $C_3$–$C_7$ secondary alkyl or $C_4$–$C_7$ tertiary alkyl groups. The position of alkyl substituents on the aryl group is not critical; for example, phenyl can be substituted at positions 1–6, naphthyl from positions 1–8, anthryl from positions 1–10, and phenanthryl from positions 1–10 substituted from 1 to 5 times with $C_1$–$C_4$ alkyl groups. It is understood that the oxygen atom illustrated in Formula XI links the chiral auxiliary to the carbonyl carbon of the compound of Formula XI and is included in Formula XI to indicate the preferred bonding position of the cyclic alkyl group to the carbonyl carbon. In a more preferred chiral auxiliary, $R_9$ and $R_{10}$ are both methyl or ethyl, and $R_{11}$ is phenyl.

In many instances it will be desirable that compound X has the stereochemical orientation of Formula

X-A

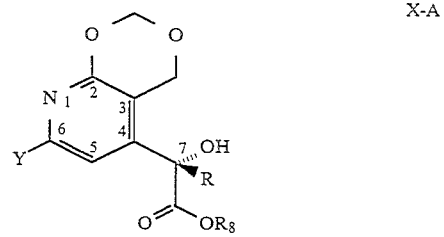

In such instances, $R_8$ should be an optically pure chiral auxiliary that will permit only the formation of diastereomers of compound X having this orientation. As used herein, an "optically pure" compound is one which contains at least 99 percent of one enantiomer of that compound. Preferred chiral auxiliaries for forming the distereomers of Formula X-A are as shown in Formula

XI-A

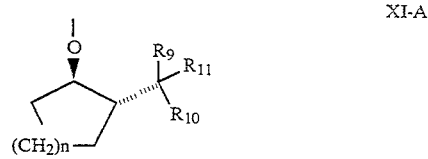

wherein R, $R_9$, $R_{10}$, and $R_{11}$ are as defined for Formula XI. As above, the oxygen atom of compound XI-A is included to show bonding position on the cyclic alkyl group and stereochemical orientation of the substituents thereon.

Scheme D begins with the commercially available pyridinol compounds of Formula V. The pyridinol of Formula V is alkylated to produce the alkoxypyridine of Formula VI. Alkylation of the oxygen at the number 2 position may be accomplished by reacting the pyridinol of Formula V with alkali metal hydride and chloromethylethyl ether. The alkylation is preferably carried out in a halogenated organic solvent such as methylene chloride, at a temperature below 0° C. and preferably below —20° C.

The compound of Formula VI is substituted at the C-3 position, halogenated and reduced to produce the 4-halo-2-alkoxy-3-hydroxyalkylpyridinol of Formula VII. Halogenation at the number 4-position may be carried out by reacting the 2-alkoxypyridine of Formula VI with an alkyllithium and an N-formyl-diamine, such as N-formyl-N,N',N'-trimethylethylenediamine, in dimethoxyethane or tetrahydrofuran to direct subsequent C-4 lithiation, and by lithiating the C-4 position of the pyridine with a suitable lithiating reagent, such as n-butyllithium. See D. Comins, et al., *J. Org. Chem* 55:69 (1990). The C-4 lithiated pyridine intermediate is preferably halogenated by adding the intermediate to a solution of iodine in a polar or nonpolar organic solvent, preferably at a temperature of at least as low as about −70° C. Subsequent to the halogenation, the halogenated intermediate is reduced with sodium borohydide to produce the 4-halo-2-alkoxy-pyridinol of Formula VII.

The compound of Formula VII is cyclized to form the 4-halo pyridyl dioxane of Formula VIII. Cyclization may be carried out by reacting the halo-alkoxy-pyridinol of Formula VII with boron trifluoride etherate. The reaction is preferably carried out in a polar or nonpolar organic solvent. Most preferably the organic solvent is methylene chloride. The halo pyridyl dioxane produced is crystalline and has a melting point of 142°-144° C.

The compound of Formula VIII is subsequently dehalogenated with a base of the formula $A^+B^-$, wherein $A^+$ is a inorganic cation, and $B^-$ is an organic anion, to form an intermediate. The intermediate is then reacted with an α-ketoester of Formula IX to form the compound of Formula X.

The base $A^+B^-$ can be any combination of an inorganic cation and an organic anion which will remove the iodo group from compound VIII to form a reactive carbanion intermediate. Exemplary inorganic cations include sodium, potassium, and lithium, with lithium being more preferred. The organic anion can be any anion which is sufficiently reactive to remove the iodo group from compound VIII but is insufficiently strong to remove substituent Y from compound VIII. Exemplary organic anions include propyl, n-butyl, phenyl, and n-pentyl, with n-butyl being preferred.

The reaction step in which the iodo group is removed from compound VIII can be carried out through the use of standard conditions for removing halogens from aromatic compounds. Preferably, this step is carried out in an inert atmosphere, such as argon or nitrogen, and in an aprotic solvent, such as tetrahydrofuran, diethyl ether, dimethoxyethane, and toluene, with tetrahydrofuran being preferred. The reaction is preferably carried out at a reduced temperature, and more preferably is carried out below 0° C.

The combination of the intermediate produced by reaction with base $A^+B^-$ and an α-ketoester of Formula IX can be carried out through the use of standard conditions for nucleophilic attack of an aromatic carbanion at an α-carbonyl carbon. Preferably, the reaction is carried out in an aprotic solvent, such as those listed above, with tetrahydrofuran being preferred, and is carried out at a reduced temperature, preferably below 0° C. In a more preferred embodiment of the process, the reacting step and the combining step are carried out in the same reaction vessel, i.e., in situ.

The α-ketoester bears the chiral auxiliary, which because of its geometric configuration, directs the nucleophilic substitution of compound VIII by compound IX to preferentially form the tertiary alcohol of compound X in one stereochemical orientation over its opposite stereochemical orientation. $R_8$ forces a preferential formation of compound X by sterically hindering the competing formation of the nonpreferred diastereomer. Exemplary chiral compounds suitable for use in the process include aryl and alkyl aryl compounds opiionally substituted from 1 to 5 times with $C_1$-$C_4$ alkyl groups, any of the compounds disclosed in U.S. Pat. No. 5,262,571 issued 16 November 1993, the subject matter of which is herein incorporated by reference, 4-phenyl-methyl-2-oxazolidine, 3-(1-naphthyl)-4,7,7-trimethyl-bicyclo [2.2.1] heptane, trans-2,5 bis(methoxymethoxymethyl)pyrrolidine, 2,10-camphorsulfamide, proline benzyl ester, pantolactone, and 4-benzyl-Z-oxazolidinone. Preferred chiral auxiliaries are compounds of Formula

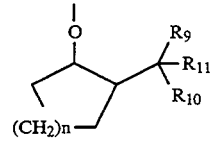

XI wherein n is 1, 2, or 3, $R_9$ is a $C_1$-$C_4$ alkyl group and $R_{10}$ is the same as $R_9$, or $R_9$ and $R_{10}$ together form cyclopentane or cyclohexane, and $R_{11}$ is selected from the group consisting of phenyl, naphthyl, anthryl, and phenanthryl optionally substituted 1 to 5 times with $C_3$-$C_7$ secondary alkyl or $C_4$-$C_7$ tertiary alkyl groups. The position of alkyl substituents on the aryl group is not critical; for example, phenyl can be substituted at positions 1-6, naphthyl from positions 1-8, anthryl from positions 1-10, and phenanthryl from positions 1-10 substituted from 1 to 5 times with $C_1$-$C_4$ alkyl groups. It is understood that the oxygen atom illustrated in Formula XI links the chiral auxiliary to the carbonyl carbon of the compound of Formula XI and is included in Formula XI to indicate the preferred bonding position of the cyclic alkyl group to the carbonyl carbon. In a more preferred chiral auxiliary, $R_9$ and $R_{10}$ are both methyl or ethyl, and $R_{11}$ is phenyl.

In many instances it will be desirable that compound X has the stereochemical orientation of Formula

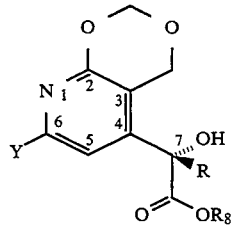

X-A

In such instances, $R_8$ should be an optically pure chiral auxiliary that will permit only the formation of diastereomers of compound X having this orientation. As used herein, an "optically pure" compound is one which contains at least 99 percent of one enantiomer of that compound. Preferred chiral auxiliaries for forming the distereomers of Formula X-A are as shown in Formula

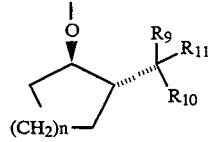

XI-A wherein R, $R_9$, $R_{10}$, and $R_{11}$ are as defined for Formula XI. As above, the oxygen atom of compound XI-A is included to show bonding position on the cyclic alkyl group and stereochemical orientation of the substitutents thereon.

The final step of Scheme D is the formation of compound III from a compound of Formula X by hydrolysis. The chiral auxiliary is removed from the compound of Formula X, the ether ring is cleaved and an ester ring is formed with the linkage at the position previously occupied by the chiral auxiliary. The ether cleavage and ester cyclization reaction may be carried out by hydrolysing the compound of Formula X with aqueous dilute inorganic acid. Preferably the inorganic acid is hydrochloric acid diluted to 10 percent. The reaction is heated at reflux for approximately 36 hours. The reaction may be carried out in a polar solvent, such as methanol, ethanol, isopropanol, etc. Preferably the solvent is methanol. The reaction produces the compounds of Formula III in crystalline form, having a melting point between about 216°–218° C.

When Y is halo in the compound of Formula III, the compound may be hydrogenated by any suitable technique, preferably by catalytic hydrogenation in the presence of a palladium catalyst in a hydrogen atmosphere under pressure (e.g., at least three atmospheres). See generally, J. March, *Advanced Organic Chemistry* 510–511 (3d. Ed. 1985).

The following examples are provided to illustrate the present invention, and should not be construed as limiting thereof. In these examples, g means grams, mg means milligrams, mol means mole, mmol means millimoles, M means Molar, mL means milliliter, min. means minute(s), hr means hour(s), mp means melting point, ° C. means degrees Centigrade, DME means dimethoxyethane, THF means tetrahydrofuran, EtOAc means ethyl acetate, and PLC means preparative thin layer chromatography.

EXAMPLE 1

Preparation of 2-chloro-6-(ethoxymethoxy)pyridine

To a solution of 13.4 g (0.1 mol) of 6-chloro-2-pyridinol in 200 mL methylene chloride at −23° C. was added 3 g sodium hydride (80%, 0.1 mol) slowly, and stirring was continued for 5 min. 10 mL of Chloromethyl ethyl ether (0.11 mol) was added dropwise at −23° C. After stirring for 15 min. at −23° C, and an additional 1 hr at room temperature, the reaction was quenched with 50 mL of water. The mixture was extracted with two 50 mL portions of methylene chloride, and the combined organic layers were washed with water and brine. After drying over sodium carbonate, the solvents were evapoated under reduced pressure. The residue was purified by radial PLC (5% ethyl acetate/hexanes) to give 7.78 g (42%) of product as a colorless oil (bp 72° C., 0.25 mmHg) and 2.14 g of recovered starting material. $^1$H NMR (300 MHz, CDCl$_3$) δ 7.55 (t, 1 H, J=7.7 Hz), 6.94 (d, 1 H, J=8.5 Hz), 6.71 (d, 1 H, J=8.0 Hz), 5.55 (s, 2 H), 3.77 (q, 2 H, J=7.1 Hz), 1.25 (t, 3 H, J=7.1 Hz). $^{13}$C NMR (75 MHz, CDCl$_3$) δ 162.4, 148.5, 141.0, 117.2, 109.3, 91.4, 65.7, 15.2. Analysis Calculated for C$_8$H$_{10}$ClNO$_2$: C, 51.21; H, 5.37; N, 7.47. Found: C, 51.33; H, 5.35; N, 7.46.

EXAMPLE 2

Preparation of 6-chloro-4-iodo-2-(ethoxymethoxy)-3-hydroxymethylpyridine

To a solution of 2.5M n-butyllithium (2.2 mL, 5 mmol) in 20 mL of THF at −10° C. was added 0.94 g 2-chloro-6-(ethoxymethoxy)pyridine (5 mmol) dropwise over 2 min. The reaction mixture was stirred for 10 min. at −10° C., then cooled to −23° C. and 0.72% N-formyl-N,N',N'-trimethylethylenediamine) was added. After stirring at −23° C. for 30 min., n-butyllithium (2.5M, 3 mL, 7.5 mmol) was added dropwise and the dark reaction mixture was stirred at −23° C. for 4 hr. The mixture was transferred via a double-tipped meedle to a solution of 1.9 g of iodine (7.5 mmol) in 10 mL of DME and 10 mL of THF at −78° C. After stirring at −78° C. for 30 min., the cooling bath was removed. 0.3 g of solid sodium borohydride (8 mmol) was added to the red mixture. 10 mL of water was added dropwise with vigorous stirring. After 30 min., the mixture was extracted with three 20-mL portions of EtOAc. The combined organic layers were washed with 20 mL of 10 percent sodium thiosulfate solution, water and brine. After drying over sodium carbonate, the solvents were removed under reduced pressure to yield the 1.3 g of crude product, which was purified by radial PLC (10% EtOAc/hexane) to give 0.7 g (40%) of pure product as a white solid, mp 43°–44° C. $^1$H NMR (300 MHz, CDCl$_3$) δ 7.43 (s, 1 H), 5.62 (s, 2 H), 4.79 (s, 2 H), 3.78 (q, 2 H, J=7.1 Hz), 2.24 (brd, 1 H), 1.26 (t, 3 H, J=7.1 Hz). $^{13}$C NMR (75 MHz, CDCl$_3$) δ 158.9, 147.8, 127.3, 124.7, 113.5, 92.0, 66.0, 63.2, 15.0. Analysis Calculated for C$_9$H$_{11}$ClNO$_3$: C, 31.47; H, 3.23; N, 4.08. Found: C, 31.68; H, 3.28; N, 4.13.

EXAMPLE 3

Preparation of 2,3-(6-chloro-4-iodopyridyl)1,3-dioxane

To a solution of 900 mg of 6-chloro-4-iodo-3-(ethoxymethoxy)-3-hydroxymethylpyridine (2.6 mmol) in 30 mL of methylene chloride at room temperature was added 0.64 mL boron trifluoride etherate (5.2 mmol). The mixture was stirred for 10 hrs at room temperature and quenched with saturated sodium bicarbonate solution. The organic layer was separated and the aqueous layer was extracted with two 10-mL portions of methylene chloride. The combined organic layers were washed with water and brine. After drying over sodium carbonate, the solvents were evaporated and the residue was recrystallized from methylene chloride/hexane to give 0.51 g (65%) of product as white needles, mp 142°–144° C. $^1$H NMR (300 MHz, CDCl$_3$) δ 7.44 (s, 1 H), 5.34 (s, 2 H), 4.66 (s, 2 H). $^{13}$C NMR (75 MHz, CDCl$_3$) δ 158.1, 148.5, 127.3, 118.2, 108.0, 92.4, 70.3. Analysis Calculated for C$_7$H$_5$ClNO$_2$: C, 28.26; H, 1.69; N, 4.71. Found: C, 28.33; H, 1.66; N, 4.71.

EXAMPLE 4

Preparation of Enantiopure 2,3-(6-chloro-4-pyridyl)1,3-dioxane

To a vigorously stirred solution of 180 mg 2,3-(6-chloro-4-iodopyridyl)1,3-dioxane (0.6 mmol) in 4 mL of THF at −100° C. under argon was added n-butyllithium (0.28 ml, 0.66 mmol). After stirring 1 min., (−)TCC-α-ketobutyrate (236 mg, 0.78 mmol) in 2 mL of THF was added over 10 sec. The mixture was stirred at −100° C. for 30 min and at ambient temperature for 30 min. The reaction was quenched with 2 mL of saturated aqueous ammonium chloride, and extracted with three 10-mL portions of EtOAc. The combined organic layers were washed with water and brine, and were dried over MgSO$_4$. Concentration afforded 360 mg (de 88%) of crude product, which was purified by radial PLC (10% EtOAc/hexanes) to give 182 mg (63%) of the hydroxyester as an oil: $^1$H NMR (300 MHz, CDCl$_3$) δ 7.23 (m, 5 H), 6.77 (s, 1 H), 5.36 (d, 1 H, J=5.8 Hz), 5.39 (d, 1 H, J=5.8 Hz), 5.01 (d, 1 H, J=15.7 Hz), 4.81 (m, 1 H), 4.75 (d, 1 H, J=15.7 Hz), 2.94 (s, 1 H), 2.2 (m, 1 H), 1.8—0.7 (m, 19 H). $^{13}$C NMR (75 MHz, CDCl$_3$) δ 171.9, 158.7, 151.4, 151.1, 147.9, 128.2, 125.2, 124.9, 116.3, 114.0, 91.6, 79.6, 79.3, 65.9, 49.1, 39.5, 32.2, 30.9, 29.5, 26.8, 25.5, 24.3, 23.8, 7.6. Analysis Calculated for $C_{26}H_{32}ClNO_5$: C, 65.88; H, 6.80; N, 2.96. Found: C, 65.99; H, 6.84; N, 3.01.

EXAMPLE 5

Preparation of enantiopure chloro DE rings

To the solution of 260 mg of the compound of Example 4 (0.538 mmol) in 2.5 mL methanol, was added 5 mL of aqueous 10 percent HCl. The mixture was heated at reflux for 36 hr, cooled to room temperature, and extracted with four 5-mL portions of 5 percent methanol/chloroform. The combined organic extracts were washed with water and brine, and were dried over magnesium sulfate. After evaporating the solvent, 20 mL of hexanes were added to the residue and the mixture was heated to reflux for 5 min. On cooling, the product precipitated and (−)−TCC remained in the hexanes. This process was repeated and the combined hexane extracts were concentrated to give 134 mg of (−)−TCC (97%). The white solid (113 mg, 86%) was recrystallized from EtOAc to give 98 mg (75%) of white crystals: mp 216°–218° C. (dec); $[\alpha]_D^{27}$ +75.5° (C 1.3, MeOH).

The foregoing is illustrative of the present invention and is not to be construed as limiting thereof. The invention is defined by the following claims, with equivalents of the claims to be included therein.

That which is claimed is:

1. A compound of Formula VIII:

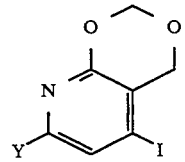

wherein Y is H or halogen.

2. A compound according to claim 1, wherein Y is H.
3. A compound according to claim 1, wherein Y is halogen.
4. A compound according to claim 1, wherein Y is fluoro.
5. A compound according to claim 1, wherein Y is chloro.
6. A compound according to claim 1, wherein Y is bromo.
7. A compound according to claim 1, wherein Y is iodo.

* * * * *